(12) United States Patent
Burki et al.

(10) Patent No.: US 11,529,177 B2
(45) Date of Patent: Dec. 20, 2022

(54) FRACTURE FIXATION PLATE FOR APPLICATION TO THE PROXIMAL HUMERUS

(71) Applicant: Bonebridge AG, Zug (CH)

(72) Inventors: Patrick Burki, Solothurn (CH); Beat Kaspar Moor, Venthône (CH); Alex Schallberger, Ennetmoos (CH); Christian Gerber, Zug (CH)

(73) Assignee: Bonebridge AG, Zug (CH)

( * ) Notice: Subject to any disclaimer, the term of this patent is extended or adjusted under 35 U.S.C. 154(b) by 0 days.

(21) Appl. No.: 17/618,315

(22) PCT Filed: Jul. 11, 2019

(86) PCT No.: PCT/CH2019/000020
§ 371 (c)(1),
(2) Date: Dec. 10, 2021

(87) PCT Pub. No.: WO2021/003583
PCT Pub. Date: Jan. 14, 2021

(65) Prior Publication Data
US 2022/0202456 A1   Jun. 30, 2022

(51) Int. Cl.
*A61B 17/80* (2006.01)
(52) U.S. Cl.
CPC ...... *A61B 17/8061* (2013.01); *A61B 17/8014* (2013.01)
(58) Field of Classification Search
CPC ............................ A61B 17/8061; A61B 17/82
See application file for complete search history.

(56) References Cited

U.S. PATENT DOCUMENTS

| 6,283,969 | B1 | 9/2001 | Grusin et al. |
| 7,335,204 | B2 | 2/2008 | Tornier |
| 2008/0119895 | A1* | 5/2008 | Manceau ........... A61B 17/8047 606/301 |
| 2009/0118768 | A1* | 5/2009 | Sixto, Jr. ................ A61B 17/17 606/301 |
| 2009/0125069 | A1 | 5/2009 | Sixto, Jr. et al. |

(Continued)

FOREIGN PATENT DOCUMENTS

EP    3178424 A1    6/2017

OTHER PUBLICATIONS

International Search Report dated Mar. 12, 2020 filed in PCT/CH2019/000020.

*Primary Examiner* — Olivia C Chang
(74) *Attorney, Agent, or Firm* — Rankin, Hill & Clark LLP

(57) ABSTRACT

The fracture fixation plate (1) is suitable for application to the proximal humerus, wherein •a) the fracture fixation plate (1) has an elongate body section (2) which has a free distal end (3) and a proximal end (4) to which there are adjoined, on each side, a right wing (5) having the center line (11) and a left wing (6) having the center line (12); •b) the body section (2) and the two wings (5, 6) are provided with a number of screw holes (7) for receiving bone-fastening elements (8), and the fracture fixation plate (1) has a bone contact face (9) and an opposite surface (10), and •c) the two wings (5, 6) have different lengths. Furthermore, •d) the two wings (5, 6) are curved, and •e) the extensions of the two curved center lines (11, 12) form an obtuse angle a.

20 Claims, 5 Drawing Sheets

(56) References Cited

U.S. PATENT DOCUMENTS

2014/0277177 A1    9/2014   Gonzalez-Hernandez
2015/0327899 A1   11/2015   Early et al.
2017/0156767 A1    6/2017   Chaudot et al.
2018/0250046 A1    9/2018   Austin et al.

* cited by examiner

FRACTURE FIXATION PLATE FOR APPLICATION TO THE PROXIMAL HUMERUS

The invention relates to a fracture fixation plate for application to the proximal humerus.

U.S. Pat. No. 6,283,969 Grusin discloses a distal radius plate with two lateral wings which, however, lie on the same straight line and do not form an angle with one another. As a result, the tubercula (*Tuberculum majus* and *Tuberculum minus*) cannot be correctly gripped.

From US 2009/0125069 Sixto et al. and US 2018/0250046 Austin et al., additional bone fixation plates are known, which, however, have the following disadvantages:
 they are adapted to the anatomic bones and not to the fractured or repositioned bones; and
 they are not optimized for use on the proximal humerus and, in particular, the shaft of the plate is too long.

The invention is intended to provide a remedy here. The underlying aim of the invention is to create a fracture fixation plate for application to the proximal humerus, which enables anatomic repositioning and refixation of the fracture fragments on the proximal humerus.

The invention achieves the posed aim with a fracture fixation plate which has the features as claimed herein.

The advantages achieved by the invention are substantially the following:
 The tubercula (*Tuberculum majus* humeri and *Tuberculum minus* humeri) can be gripped laterally and medially, so that, a downward escape of the head is prevented; and the excessive repositioning of the calcar during repositioning is prevented by the geometry of the bone fixation plate.

Figure 1:
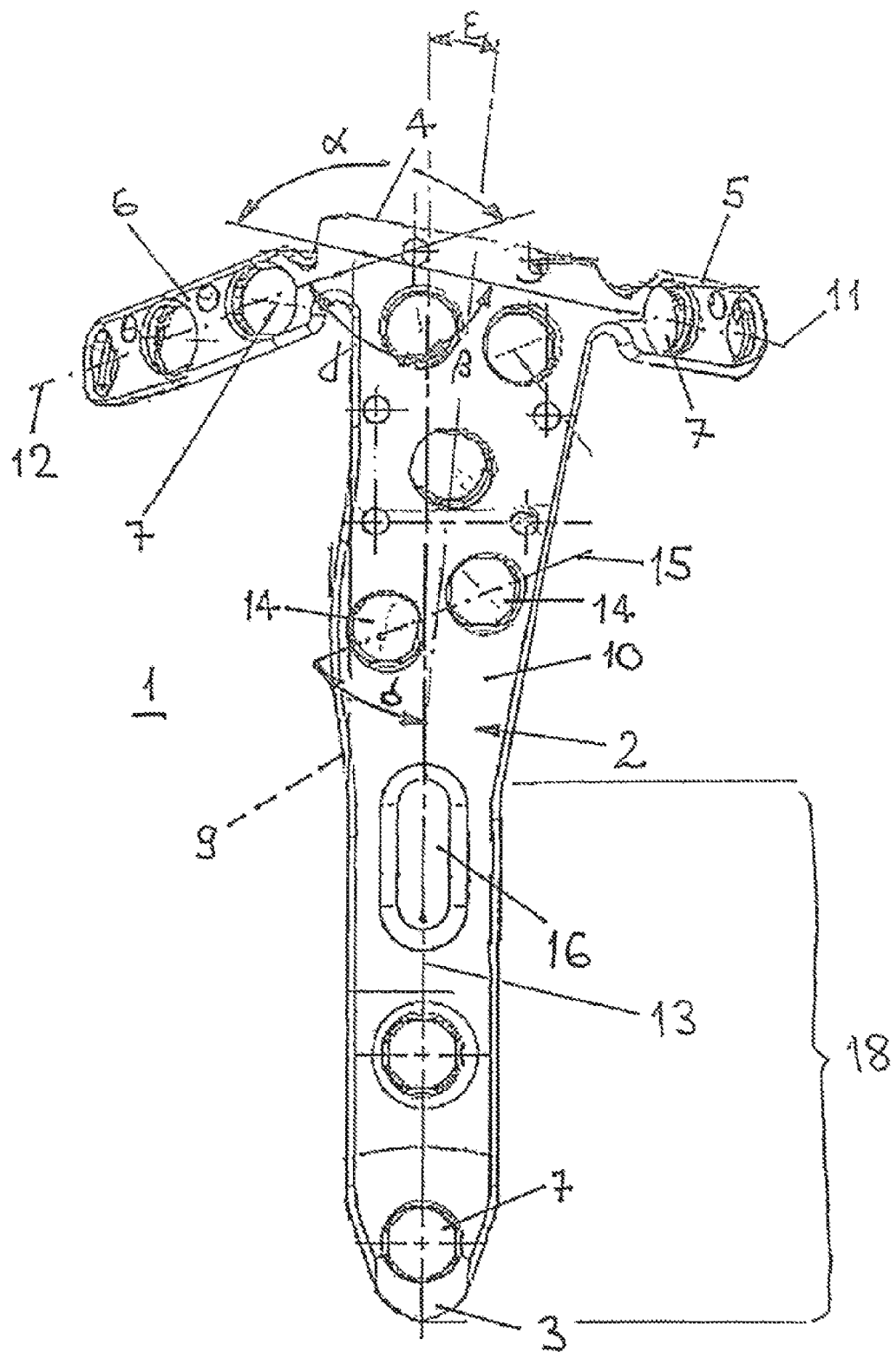

The posed aim is achieved by the invention with a fracture fixation plate as claimed herein. Additional advantageous designs of the invention can be commented on as follows:

In a particular embodiment of the fracture fixation plate 1, the angle $\alpha < 175°$ and is preferably in the range from 110° to 160°. The angle $\alpha$—as represented in FIG. 1—is measured between the proximally extended center lines 11, 12 of the two wings 5, 6.

The two wings 5, 6 can have a circular cylindrical curvature. Here, the two wings 5, 6 can have the same curvature, preferably the same circular cylindrical curvature.

In an additional embodiment, the center lines 11, 12 have a helical curvature.

The distal section 18 of the body section 2 can define a longitudinal center line 13 which intersects the plane in which the curved center line 11 of the right wing 5 lies, at an angle $\beta \neq 90°$. The angle $\beta$ can advantageously be in the range between 60° and 85°.

The distal section 18 of the body section 2 can define a longitudinal center line (13) which intersects the plane in which the curved center line 12 of the left wing (6) lies, at an angle $\gamma \neq 90°$. The angle $\gamma \neq 90°$ is advantageously in the range from 50° to 80° t.

In a particular embodiment, the left wing 6 is angled more strongly than the right wing 5, so that $\gamma < \beta$. This embodiment was found to be optimal for a secure gripping of the *Tuberculum majus* and the *Tuberculum minus* of the humeral head.

The proximal end (4) of the body section 2 and the two wings 5, 6 can be flush. Thereby, the proximal end of the bone fixation plate assumes a less distal position, so that a jamming in in the acromion (impingement) is prevented.

The elongate body section 2 of the fracture fixation plate can have a number of threaded holes 14 which are arranged offset with respect to the longitudinal center line 13. This embodiment has the advantage that the bone fixation plate becomes narrower and thus the contact surface on the bone is reduced.

The connecting line 15 between the center points of two such threaded holes 14 arranged offset can intersect the longitudinal center line 13 at an angle $\delta \neq 90°$. This arrangement of the threaded holes enables the introduction of calcar screws with a clearly smaller width of the bone fixation plate in comparison to the prior art.

The angle $\delta$ is advantageously in the range from 10° to 70°.

The center axis of one or more of the threaded holes 14 arranged offset can intersect the plane formed by the body section 2 at an angle $\varepsilon \neq 90°$, and the angle c can preferably be in the range from 3° to 10°.

In an additional embodiment, the body section 2 can additionally have an elongate compression hole 16.

In a particular embodiment, the ratio between the length L of the left wing 6 and the length l of the right wing (5) satisfies the condition $L \geq 1.21$.

In an additional embodiment, the longitudinal center line 13 intersects the plane in which the curved center line of the left wing lies, at an angle $\beta_{LH} \neq 90°$. The angle $\beta_{LH}$ is advantageously in the range between 60° and 85°.

In an additional embodiment, the longitudinal center line 13 intersects the plane in which the curved center line of the right wing lies, at an angle $\gamma_{LH} \neq 90°$. The angle $\gamma_{LH} \neq 90°$ is advantageously in the range from 50° to 80°.

In a particular embodiment, the condition $\gamma_{LH} \leq \beta_{LH}$ applies.

According to an additional embodiment, the length of the right wing is greater than or equal to 1.2 times the length of the left wing.

The fracture fixation plate 1 according to the invention is suitable, in particular, for treating bone fractures of the proximal humerus.

The invention and developments of the invention are explained in further detail below in reference to the partially diagrammatic representations of multiple embodiment examples.

Figure 2:
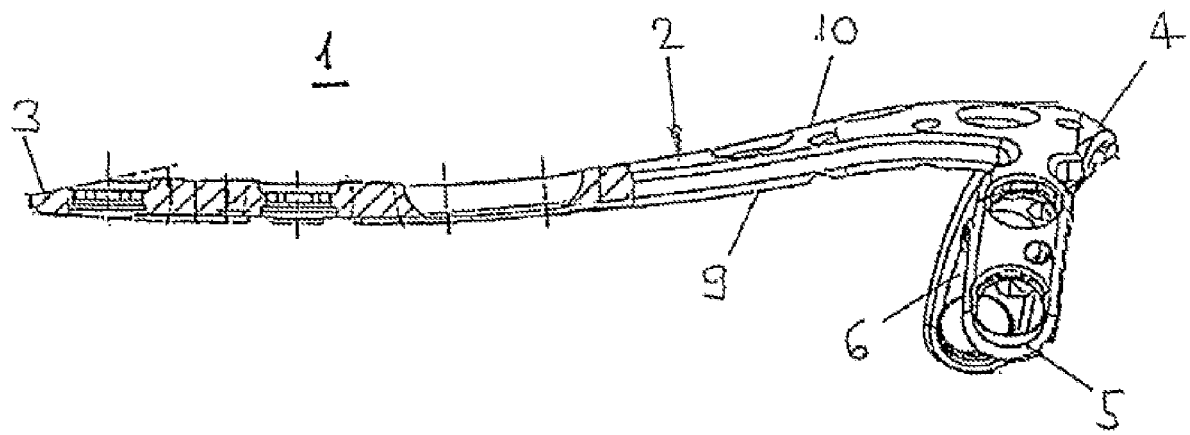
Figure 3:
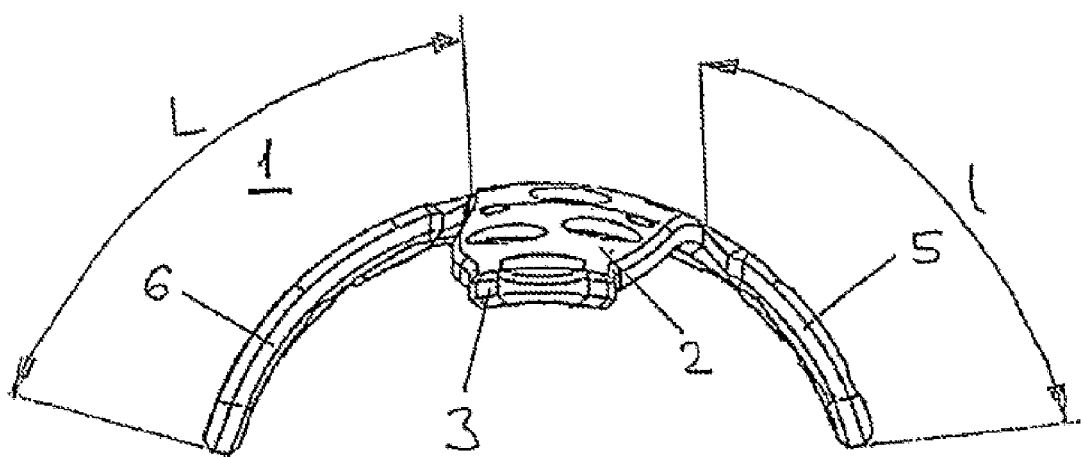
Figure 4:
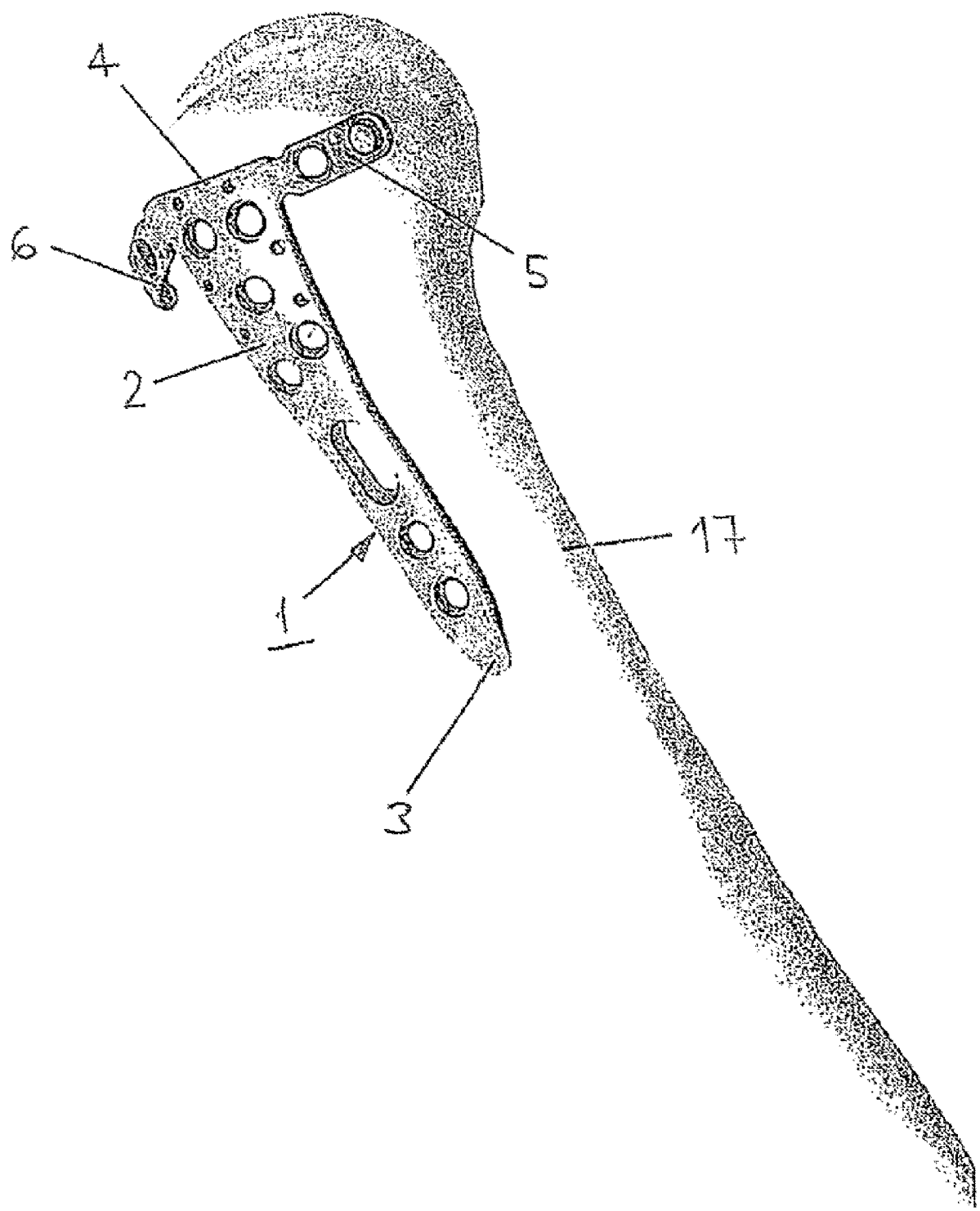
Figure 5:
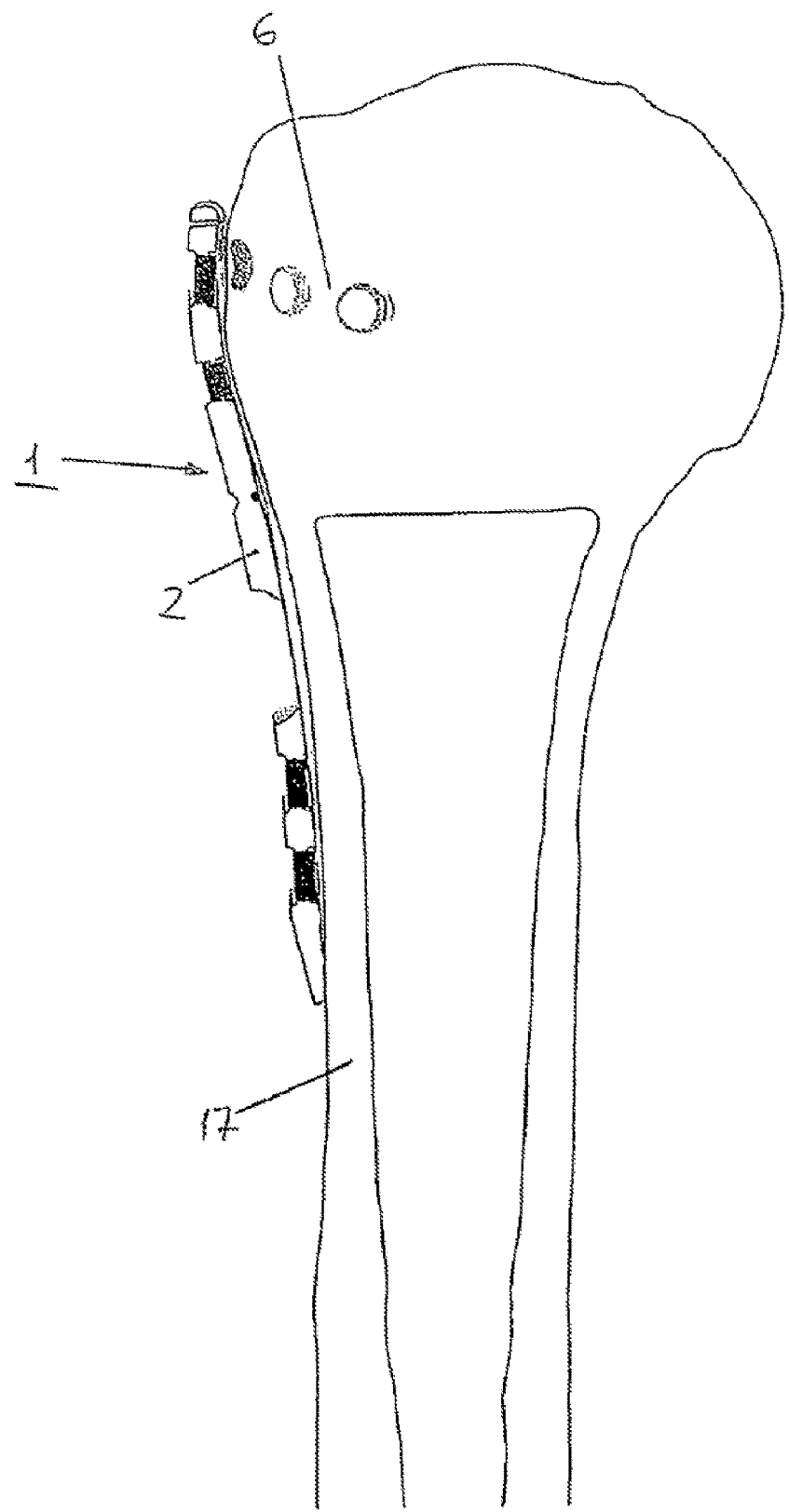
Figure 6:
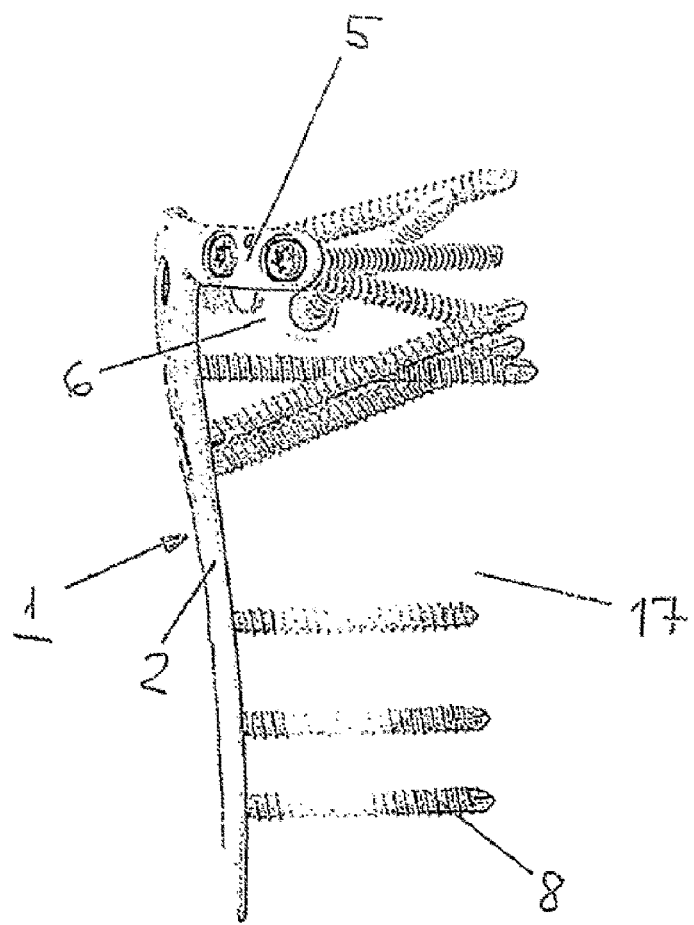
Figure 7:
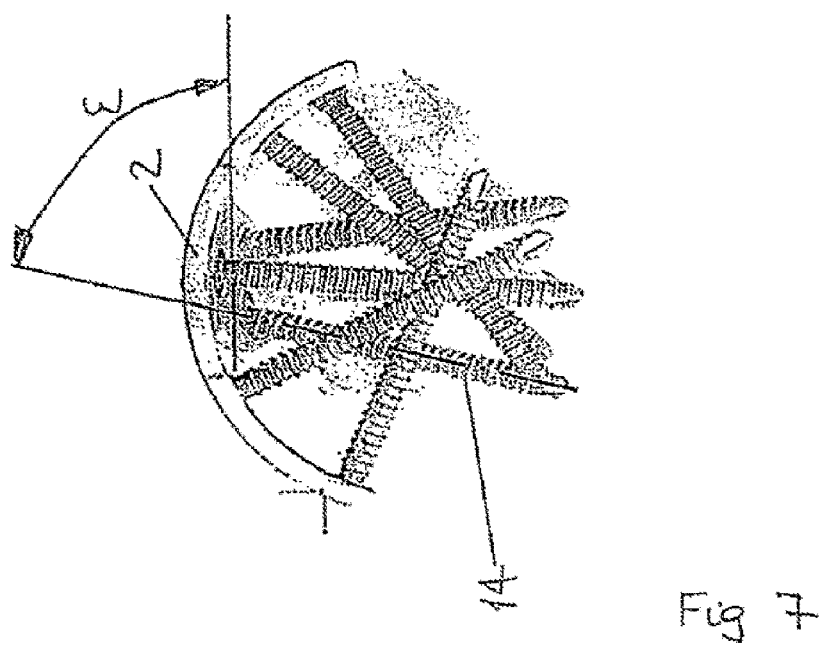

The figures show:

FIG. 1, a view onto the upper side of an embodiment of the fracture fixation plate according to the invention for the left humerus;

FIG. 2, a side view of the embodiment of the fracture fixation plate according to the invention represented in FIG. 1;

FIG. 3, a distal to proximal view of the embodiment of the fracture fixation plate according to the invention represented in FIG. 1;

FIG. 4, a perspective view of the embodiment represented in FIG. 1, placed on the proximal lateral humerus;

FIG. 5, a longitudinal section through the fractured fixation plate represented in FIG. 4;

FIG. 6, a lateral perspective view of the fracture fixation plate represented in FIG. 5, after screwing onto the proximal humerus has occurred; and FIG. 7, a cranial perspective view of the screwed fracture fixation plate represented in FIG. 6.

The embodiment of the fracture fixation plate 1 according to the invention represented in FIGS. 1 to 7 has a longitudinal center line 13 and substantially comprises an elongate body section 2 which has a free distal end 3 and a proximal end 4. The elongate body section 2 comprises, for example and in a nonlimiting manner, a proximal subsection comprising the proximal end 4 and a distal subsection comprising the distal end 3, wherein the proximal body section is slightly angled with respect to the distal body section by an angle ε. Furthermore, on each side, a right wing 5 with center line 11 and a left wing 6 with center line 12 are adjoined to the proximal end 4.

Optimal values for the length of the elongate body section 2 are 8-14 cm depending on the embodiment.

The two wings 5, 6 have different lengths and are curved, wherein the extensions of the two curved center lines 11, 12 intersect at an angle α. The angle α is, for example and in a nonlimiting manner, between 110° and 160°. The ratio between the length L of the left wing 6 (FIG. 3) and the length 1 of the right wing 5 satisfies the condition L≥1.2 1. The two wings 5, 6 have a circular cylindrical curvature, wherein the center lines 11, 12 have a helical curvature. The two wings 5, 6 have, for example and in a nonlimiting manner, the same circular cylinder curvature. The two wings 5, 6 and the proximal end 4 of the body section 2 are flush.

The longitudinal center line 13 intersects the plane in which the curved center line 11 of the right wing 5 lies, for example and in a nonlimiting manner, at an angle β in a range between 60° and 85°. Furthermore, the longitudinal center line 13 intersects the plane in which the curved center line 12 of the left wing 6 lies, for example and in a nonlimiting manner, at an angle γ between 50° and 80°. Here, the left wing 6 is angled more strongly than the right wing 5, so that γ≤β.

The fracture fixation plate 1 has a bone contact face 9 and an opposite surface 10. The body section 2 and the two wings 5, 6 are provided with a number of screw holes 7 for receiving bone fastening elements 8 (FIG. 6).

Furthermore, the elongate body section 2 comprises, for example and in a nonlimiting manner, five threaded holes 14 which are arranged offset with respect to the longitudinal center line 13, wherein the connecting line 15 between the center points of two such threaded holes 14 arranged offset intersects the longitudinal center line 13, for example and in a nonlimiting manner, at an angle δ between 10° and 70°. For example and in a nonlimiting manner, the center axis of these two threaded holes 14 arranged offset intersects the plane formed by the body section 2 at an angle ε≠90°. In addition, the body section 2 comprises an elongate compression hole 16.

In FIGS. 1 to 7, an embodiment for the left humerus is represented. For the right humerus, mirror-image embodiments are provided, wherein an embodiment for the right humerus differs from the embodiment for the left humerus represented in FIGS. 1 to 7 only in that:

the ratio between the length $L_{LH}$ of the left wing and the length $l_{LH}$ of the right wing satisfies the condition $L_{LH} \leq 1.2\, l_{LH}$;

the longitudinal center line intersects the plane in which the curved center line of the left wing lies, for example and in a nonlimiting manner, at an angle $\beta_{LH}$ which is in a range between 60° and 85°;

the longitudinal center line intersects the plane in which the curved center line of the right wing lies, for example and in a nonlimiting manner, at an angle $\gamma_{LH}$ which is between 50° and 80°; and the right wing is angled more strongly than the left wing.

Although there are different embodiments of the present invention, as described above, they should be understood in the sense that the different features can be used both individually and in any desired combination.

Therefore, this invention is not simply limited to the above-mentioned particularly preferred embodiments.

The invention claimed is:

1. A fracture fixation plate for application to a proximal humerus bone wherein:
   the fracture fixation plate has an elongate body section which has a free distal end and a proximal end;
   a right wing extends from a right side of the elongate body section at the proximal end;
   a left wing extends from a left side of the elongate body section at the proximal end;
   the elongate body section and the right and left wings are provided with screw holes for receiving bone-fastening elements;
   the fracture fixation plate has a bone contact face and an opposite surface;
   the right and left wings have different lengths;
   the right and left wings each have a curvature; and
   the right and left wings are swept wings, which sweep towards the distal end of the elongate body section; and
   wherein center lines of the right and left wings have a helical curvature.

2. A fracture fixation plate for application to a proximal humerus bone, wherein:
   the fracture fixation plate has an elongate body section which has a free distal end and a proximal end;
   a right wing extends from a right side of the elongate body section at the proximal end;
   a left wing extends from a left side of the elongate body section at the proximal end;
   the elongate body section and the right and left wings are provided with screw holes for receiving bone-fastening elements;
   the fracture fixation plate has a bone contact face and an opposite surface;
   the right and left wings have different lengths;
   the right and left wings each have a curvature; and
   the right and left wings are swept wings, which sweep towards the distal end of the elongate body section; and
   wherein a first plane, in which a center line of the right wing lies, and a second plane, in which a center line of the left wing lies, intersect at an obtuse angle α opening in a direction toward the distal end of the elongated body section.

3. The fracture fixation plate according to claim 2, wherein the angle α<175°.

4. The fracture fixation plate according to claim 2, wherein the right and left wings each have a circular cylindrical curvature.

5. The fracture fixation plate according to claim 2, wherein the right and left wings have the same curvature.

6. The fracture fixation plate according to claim 2, wherein a distal section of the elongate body section defines a longitudinal center line which intersects the first plane at an angle β≠90°.

7. The fracture fixation plate according to claim 6, wherein the angle β is in the range between 60° and 85°.

8. The fracture fixation plate according to claim 2, wherein a distal section of the elongate body section defines a longitudinal center line which intersects the second plane at an angle Y≠90°.

9. The fracture fixation plate according to claim 8, wherein the angle Y≠90° is in the range from 50° to 80°.

10. The fracture fixation plate according to claim 6, wherein the longitudinal center line intersects-a the second plane at an angle Y≠90°, and wherein Y<β.

11. The fracture fixation plate according to claim 6, wherein the proximal end of the elongate body section and the left and right wings are flush.

12. The fracture fixation plate according to claim 6, wherein the elongate body section has two or more threaded holes which are arranged offset with respect to the longitudinal center line.

13. The fracture fixation plate according to claim 12, wherein a connecting line between center points of two of the two or more threaded holes which are arranged offset intersects the longitudinal center line at an angle $\delta \neq 90°$.

14. The fracture fixation plate according to claim 13, wherein the angle $\delta$ is in the range from 10° to 70°.

15. The fracture fixation plate according to claim 12, wherein at least one of the two or more threaded holes which are arranged offset has a center axis that intersects a plane containing the longitudinal center line of the elongate body section at an angle $\varepsilon \neq 90°$.

16. The fracture fixation plate according to claim 2, wherein the elongate body section further comprises an elongate compression hole.

17. The fracture fixation plate according to claim 2, wherein the left wing has a length $L_L$, wherein the right wing has a length $L_R$, and wherein $L_L \geq 1.2\, L_R$.

18. The fracture fixation plate according to claim 11, wherein the longitudinal center line intersects the second plane in which the curved center line of the left wing lies, at an angle $\beta_{LH} \neq 90°$.

19. The fracture fixation plate according to claim 18, wherein the angle $\beta_{LH}$ is in the range between 60° and 85°.

20. A method for treating a fracture of the proximal humerus bone, the method comprising:
 applying a fracture fixation plate according to claim 2 across the fracture of the proximal humerus bone; and
 inserting bone-fastening elements through the screw holes of the facture fixation plate and into the proximal humerus bone.

\* \* \* \* \*

UNITED STATES PATENT AND TRADEMARK OFFICE
CERTIFICATE OF CORRECTION

PATENT NO. : 11,529,177 B2
APPLICATION NO. : 17/618315
DATED : December 20, 2022
INVENTOR(S) : Patrick Burki et al.

It is certified that error appears in the above-identified patent and that said Letters Patent is hereby corrected as shown below:

In the Claims

In Column 4, Line 63, delete "-a" between --intersects-- and --the--

Signed and Sealed this
Sixth Day of February, 2024

Katherine Kelly Vidal
*Director of the United States Patent and Trademark Office*